United States Patent

Fukuyama et al.

Patent Number: 5,086,124
Date of Patent: Feb. 4, 1992

[54] HIGH HEAT DISTORTION TEMPERATURE EPOXY SILOXANE/ORGANIC EPOXY COMPOSITIONS

[75] Inventors: James M. Fukuyama, Clifton Park; Julia L. Lee, Schenectady, both of N.Y.

[73] Assignee: General Electric Company, Waterford, N.Y.

[21] Appl. No.: 548,156

[22] Filed: Jul. 5, 1990

[51] Int. Cl.$^5$ ............................................... C08L 71/02
[52] U.S. Cl. ............................................ 525/403; 528/27
[58] Field of Search ............................................ 525/403

[56] References Cited

U.S. PATENT DOCUMENTS 4,138,255  2/1979  Crivello ........................... 96/35.1
4,275,190  6/1981  Dudgeon .......................... 528/361

OTHER PUBLICATIONS

U.S. patent application Ser. No. 07/640,503 (copending and commonly assigned), to Eckberg et al., Filed 1/14/91, which is a file wrapper continuation of U.S. patent application Ser. No. 07/331,219, Filed 3/30/89, now abandoned.

Primary Examiner—Melvyn I. Marquis
Assistant Examiner—D. E. Aylward

[57] ABSTRACT

A heat curable cyclic epoxy siloxane/organic opoxy resin blend which will polymerize to form a composition having a high heat distortion temperature, the blend comprising:
- (A) a tetraorganotetraepoxy cyclic siloxane monomer;
- (B) an organic epoxy resin, the ratio of parts of (A) to parts of (B) being from about 10:1 to about 1:1;
- (C) from about 2.5 to about 3.0 weight percent, based on the combined weight of (A) and (B), of a cationic onium salt catalyst; and
- (D) from about 0.25 to about 0.30 weight percent, based on the combined weight of (A) and (B), of a copper salt cocatalyst.

15 Claims, No Drawings

HIGH HEAT DISTORTION TEMPERATURE EPOXY SILOXANE/ORGANIC EPOXY COMPOSITIONS

BACKGROUND OF THE INVENTION

The present invention is directed to heat curable blends of organic epoxy resins and cyclic epoxy siloxane monomers. More particularly, the present invention is directed to heat curable blends of organic epoxy resins and tetraorganotetraepoxy cyclic siloxane monomers which polymerize to form compositions having high heat distortion temperatures.

Blends of epoxy silicones and organic epoxy compounds are known in the art. Reference is made, for example, to U.S. Pat. No. 4,138,255 to Crivello and to copending, commonly assigned application Ser. No. 07/331,219 to Eckberg et al. (Eckberg), filed Mar. 30, 1989.

U.S. Pat. No. 4,138,255 to Crivello discloses a method for effecting the cationic polymerization of an epoxy resin by exposing a mixture of epoxy resin and an aromatic Group VIa onium salt to radiant energy. It is disclosed in Crivello at column 3, line 54 that the epoxy resin may be composed of a mixture of epoxy monomers, epoxy prepolymers, and oxirane containing organic polymers. It is further disclosed at column 4, lines 21-22 that epoxy siloxanes can be used as the epoxy resin.

Copending, commonly assigned application Ser. No. 07/331,219 to Eckberg et al. (Eckberg) discloses a photopolymerizable coating composition containing an organic cycloaliphatic polyepoxide, a cure accelerating amount of a cycloaliphatic epoxy-functional siloxane, and a catalytic amount of a photocatalyst. The photocatalyst can be an aromatic iodonium complex salt.

The present invention is based on the discovery that a polymerizable organic epoxide composition containing certain epoxy siloxane monomers will polymerize to form compositions having heat distortion temperatures which are higher than those obtained for compositions prepared from polymerizable compositions containing organic epoxides alone or in combination with other epoxy siloxane monomers.

The epoxy siloxane monomers used in the invention were disclosed in copending, commonly assigned application Ser. No. 07/391,761 to Crivello et al. (Crivello), filed Aug. 9, 1989. Although Crivello discloses the thermal cationic polymerization of these monomers in the presence of an onium salt and a copper co-catalyst, Crivello does not disclose the combination of these epoxy siloxane monomers with organic epoxide compounds, or the criticality of the amount of onium salt catalyst to the heat distortion temperature of the polymerized composition.

SUMMARY OF THE INVENTION

The present invention is directed to a heat curable cyclic epoxy siloxane/organic epoxy resin blend which will polymerize to form a composition having a high heat distortion temperature, the blend comprising:

(A) a tetraorganotetraepoxy cyclic siloxane monomer having the general formula

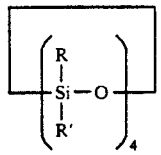

wherein each R group is, independently, a monovalent substituted or unsubstituted $C_{1-12}$ alkyl, $C_{1-12}$ cycloalkyl, or phenyl radical; each R' group is, independently, R, a monovalent $C_{2-12}$ alkyl radical, or a monovalent epoxy functional group having 2-10 carbon atoms with the proviso that at least one of the R' groups is epoxy functional;

(B) an organic epoxy resin, the ratio of parts of (A) to parts of (B) being from about 4:1 to about 1:1;

(C) from about 2.5 to about 3.0 weight percent, based on the combined weight of (A) and (B), of an onium salt catalyst; and (D) from about 0.25 to about 0.30 weight percent, based on the combined weight of (A) and (B), of a copper salt cocatalyst.

The present invention is further directed to the high heat distortion temperature epoxy siloxane/organic epoxy composition prepared from the thermal polymerization of the heat curable composition described above. In addition, the present invention is directed to a method for preparing an epoxy siloxane/organic epoxy composition having a high heat distortion temperature by blending an organic epoxy resin with the epoxy siloxane monomers described above and thermally polymerizing the resulting mixture in the presence of a critical amount of an onium salt catalyst and a copper salt co-catalyst.

The compositions prepared in the present invention are useful in such applications as coatings or high temperature formulations where high heat distortion temperatures are required or desired.

DETAILED DESCRIPTION OF THE INVENTION

Component (A) of the composition of the present invention is a cyclic epoxy functional siloxane monomer having the general formula

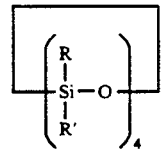

wherein each R group is, independently, a monovalent substituted or unsubstituted $C_{1-12}$ alkyl, $C_{1-12}$ cycloalkyl, or phenyl radical; and each R' group is, independently, R, a monovalent $C_{2-12}$ alkyl radical, or a monovalent epoxy functional group having 2-10 carbon atoms with the proviso that at least one of the R' groups is epoxy functional.

R is preferably methyl and R' is preferably a cycloaliphatic epoxy group and, most preferably, a cycloaliphatic epoxy group derived from 3-vinyl-7-oxabicyclo[4.1.0]heptane.

It is also contemplated that the hydrogen atoms on the R groups may be halogen substituted, preferably fluorine. Thus, one embodiment of this invention will have R defined as $C_{1-12}$ haloalkyl, preferably fluoroalkyl. More preferably, in the case of halo substitution, R would be defined as trifluoropropyl.

The monomer used as component (A) in this invention can be prepared according to the method taught in copending, commonly assigned Application Ser. No. 391,761 to Crivello et al. (Crivello), filed Aug. 9, 1989, which is incorporated by reference herein.

In the Crivello method, the cyclic epoxy functional siloxane monomer of formula (I) above is obtained by hydrosilation of a cyclic silicone hydride, specifically, a tetrahydrogen tetraorgano cyclotetrasiloxane, with ethylenically unsaturated organic epoxides or with mixtures of ethylenically unsaturated organic epoxides and ethylenically unsaturated organic compounds. The ethylenically unsaturated species of the epoxides and/or epoxide/organic mixture react with the silicone hydride via addition reaction in the presence of a precious metal catalyst, such as platinum, to produce a siloxane with epoxy functionality. Such hydrosilation reactions are taught in U.S. Pat. No. 4,743,377 (Ohtsu et al.), herein incorporated by reference.

The cyclic silicone hydride which can be used to prepare the monomer of formula (I) is well known and may be produced, for instance, by the hydrolysis and condensation of hydrolyzable organosilicon compounds, e.g. dichlorodimethylsilane and dichlorohydrogenmethylsilane. The cyclic silicone hydride may also be obtained by equilibrating polyorganosiloxanes and polyorganohydrogensiloxanes in the presence of strong acids. Such cyclic silicone hydrides are well known in the art and may be represented by the formula:

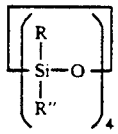

(II)

wherein R is as previously defined, and each R" group is, independently, R or hydrogen with the proviso that at least one of the R" groups is hydrogen. Such cyclic silicone hydrides are disclosed in U.S. Pat. No. 4,743,377 (Ohtsu et al.), herein incorporated by reference.

The ethylenically unsaturated organic epoxides, which may react to form the epoxy-functional R' groups disclosed above, are any vinyl- or allyl-functional epoxides which will undergo addition reactions with SiH-functional groups. Preferably, the epoxides are vinyl functional cycloaliphatic epoxides. Most preferably, the vinyl functional epoxide is 3-vinyl-7-oxabicyclo[4.1.0]heptane and is represented by the following formula:

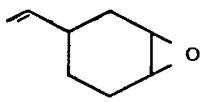

(III)

Additional ethylenically unsaturated epoxides which will react to form the R' groups above that have been found to be useful in this invention include 3-isopropenyl-6-methyl-7-oxabicyclo[4.1.0]-heptane (limonene monoxide); 3,4-epoxy-1-butene (butadiene monoxide); 5,6-epoxy-1-hexene; 7,8-epoxy-1-octene; 11,12-epoxy-1-dodecene; etc.

The ethylenically unsaturated organic compounds which also may be used to form the R' groups are any substituted or unsubstituted hydrocarbon of from 2 to 12 carbon atoms having one double bond per molecule. If there is more than one double bond, premature crosslinking between different molecules of the hydride will occur resulting in the formation of gels. It is preferable that the double bond be on the terminal group of the organic compound. The physical properties of the final, cured product may be varied by varying the chain length of the organic group. As chain length increases, hardness decreases, and tensile, elongation, and modulus increases.

The hydrosilation catalyst which may be used to effect the addition of the ethylenically unsaturated epoxide or epoxide/organic mixture may be any suitable precious metal catalyst, preferably platinum. Such catalysts are well known in the art. Preferred catalysts are taught by Lamoreaux in U.S. Pat. No. 3,917,432; 3,197,433; and 3,220,972; hereby incorporated by reference. The platinum catalyst disclosed in the patents to Lamoreaux is a complex formed from chloroplatinic acid with up to 2 moles per gram of platinum of a member selected from the class consisting of alcohols, ethers, aldehydes, and mixtures of the above. This catalyst will sometimes be referred to herein as the "Lamoreaux catalyst".

In order to produce the cyclic epoxy siloxane monomer used in this invention, it is important to remove the traces of water from the reaction in order to prevent premature crosslinking and the subsequent formation of gels.

Component (B) of the composition of this invention is an organic epoxy resin. The term "epoxy resin" as used herein includes any monomeric, dimeric, oligomeric, or polymeric epoxy material containing one or a plurality of epoxy functional groups. For example, those resins which result from the reaction of bisphenol A (4,4'-isopropylidenediphenol) and epichlorohydrin, or by the reaction of low molecular weight phenol-formaldehyde resins (Novolak resins) with epichlorohydrin, can be used alone or in combination with an epoxy containing compound as a reactive diluent. Such diluents as phenyl glycidyl ether, 4-vinylcyclohexene dioxide, limonene dioxide, 1,2-cyclohexene oxide, glycidyl acrylate, glycidyl methacrylate, styrene oxide, allyl glycidyl ether, and the like, may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers.

The ratio of parts of (A) to parts of (B) is from about 10:1, preferably about 4:1, and most preferably about 1:1.

Component (C) of the composition of this invention is a cationic onium salt catalyst. The onium salt catalyst generally has the formula:

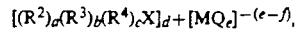

wherein $R^2$ is a monovalent aromatic organic radical, $R^3$ is a monovalent organic aliphatic radical selected from alkyl, cycloalkyl and substituted alkyl, $R^4$ is a polyvalent organic radical forming a heterocyclic or fused ring structure selected from aliphatic radicals and aromatic radicals, X is a Group VIa element selected from sulfur, selenium and tellurium, M is a metal or metalloid, Q is a halogen radical, a is a whole number equal to 0 to 3 inclusive, b is a whole number equal to 0 to 2 inclusive, c is a whole number equal to 0 or 1 where the sum of a+b+c is a value equal to 3 or the valence of X, d=e−f, f=valence of M and is an integer equal to from 2 to 7 inclusive, e is greater than f and is an integer having a value up to 8. Such salts may be selected from the group consisting of diaryliodonium salts, triarylsulfonium salts, aryldiazonium salts, ferrocenium salts, diarylsulfoxonium salts, triarylsulfoxonium salts, dialkylphenacylsulfonium salts, dialkylhydroxyphenylsulfonium salts, phenacyltriaryl-phosphonium salts, and phenacyl salts of heterocyclic nitrogen-containing compounds. Such catalysts are taught in U.S. Pat. Nos. 4,310,469 (Crivello); 4,175,972 (Crivello); 4,138,255 (Crivello); and 4,058,401 (Crivello), each of which are incorporated by reference herein.

Preferably, the onium salt is a diaryliodonium salt, and most preferably it is (4-octyloxyphenyl) phenyliodonium hexafluoroantimonate.

It is critical to the present invention that the onium salt catalyst be used in an amount within the range of from about 2.5 to about 3.0 mole percent, and preferably about 2.5 mole percent, based on the weight of component (A). At levels less than about 2.5 mole percent, low heat distortion temperatures were obtained, while at levels greater than about 3.0 mole percent, cracking of the cured samples occurred upon cooling.

Component (D) of the composition of the present invention is a copper salt cocatalyst. The copper salts which can be used in the practice of this invention include, for example, copper (I) salts such as copper halides, e.g., Cu(I) chloride, Cu(I) bromide, and the like; and copper (II) salts, such as Cu(II) benzoate, Cu(II) acetate, Cu(II) stearate, Cu(II) gluconate, Cu(II) citrate, Cu(II) formate, Cu(II) oleate, Cu(II) carbonate, and the like. Preferably, the copper salt cocatalyst used in this invention is copper stearate.

The copper salt cocatalyst is used in an amount within the range of from about 0.25 to about 0.30 mole percent, and preferably about 0.25 mole percent.

The composition of this invention may optionally contain a reducing agent which is any organic or inorganic compound or polymer capable of lowering or reducing the charge of the hetero atom of the diaryliodonium salt. Suitable reducing agents are disclosed, for example, in U.S. Pat. No. 4,239,725 (Crivello), which was previously incorporated by reference herein. Examples of suitable reducing agents include ascorbic acid and its derivatives, e.g., ascorboyl palmitate, ascorboyl oleate, and the like; tin compounds, e.g., Sn+2 carboxylic acid salts, such as stannous octoate, stannous stearate, and the like; alpha-hydroxy compounds, and iron compounds.

The polymerizable composition used in the present invention can be prepared by effecting contact between components A-D and, optionally, the other ingredients described above as suitable additives.

The composition is polymerized by heating the mixture of ingredients at a temperature and a time sufficient to effect polymerization. In general, the polymerization is carried out at a temperature of from about 120° C. to about 170° C. and for a time period of from about 30 minutes to about 2 hours. The time required to effect polymerization depends upon a number of factors such as the particular reactants and the amount of catalyst and cocatalyst used.

In order that those skilled in the art will be better able to practice the invention, the following examples are given by way of illustration and not by way of limitation.

EXPERIMENTAL

In the examples below, the term "$D_4^E$" refers to a cyclic epoxy monomer having the formula

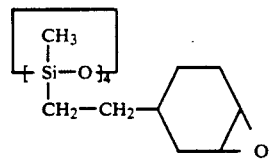

The term "$D_n^E$" refers to a cyclic epoxy siloxane monomer having the formula:

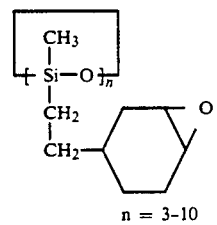

n = 3–10

The term "$M_2^E$" refers to an epoxy siloxane monomer having the formula:

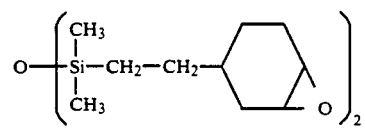

The term "$D_2^E D_2$" refers to an epoxy siloxane monomer having the formula:

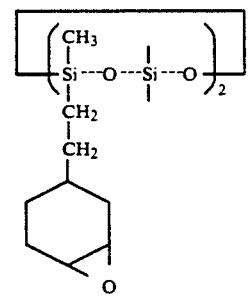

The term "$D_5^E$" refers to a cyclic epoxy siloxane monomer having the formula

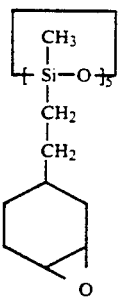

EXAMPLE 1

The cyclic tetramer, $D_4^E$, was prepared in the following manner.

Into a 100 mL three necked round bottom flask equipped with a magnetic stirrer, a Dean Stark trap containing CaH$_2$, drying tube, nitrogen inlet, and reflux condenser were placed 52.1 g (0.42 mol) distilled 3-vinyl-7-oxabicyclo[4.,1.0]heptane and 24 g (0.1 mol) 2,4,6,8-tetramethylcyclotetrasiloxane ($D_4^H$) which had been dried over CaH$_2$ and then u fractionally distilled under reduced pressure. There were also added 80 mL toluene and the reaction mixture refluxed through the trap for 2 hours. The reaction mixture was cooled and 2 drops of the Lamoreaux catalyst was added. The reaction mixture was gradually warmed under a nitrogen blanket to 50°°-55° C. and maintained at that temperature for 3 hours. After standing overnight, the IR of the reaction mixture showed the absence of a band at 2100 cm$^{-1}$. The solvent and excess epoxide starting material were removed under vacuum. There were obtained 52 g (87% yield) of cyclic tetrameric epoxide product.

EXAMPLE 2

The cyclic epoxy-siloxane, $D_2^E D_2$, was prepared as follows.

A mixture (20 g) containing the following proportions of cyclic oligomers: 85.3% $D_2^H D_2$, 7.5% $D_3^H D$ and 6.5% $D^H D_3$ (where D indicates a dimethylsiloxy group and $D^H$ indicates a methylhydrogensiloxy group; the subscript denotes the number of those groups in the ring) was placed into a 250 mL round bottom flask equipped with a magnetic stirrer, reflux condenser and nitrogen inlet. To this mixture was added 20 g (0.16 mol) 3-vinyl-7-oxabicyclo[4.10]heptane, 150 mL toluene. The reaction mixture was dried by azeotropic distillation through a CaH$_2$ trap for 1.5 hours, cooled and two drops of the Lamoreaux catalyst added. The temperature was raised to 50° C. for 1.5 hours., at that time the IR showed the absence of the 2100 cm$^{-1}$ band ascribed to the Si-H bond. The mixture was stirred overnight at room temperature and then the toluene and excess epoxy compound removed on a rotary evaporator. Lastly, the mixture of epoxy compounds was subjected to high vacuum stripping at 50° C.

EXAMPLE 3

The mixture of cyclic epoxy-siloxane monomers, $D_n^E$, was prepared as follows. Dichloromethylsilane (34.3 g., 0.298 mol) and methylene chloride (250 mL) were mixed together in a 500 mL round-bottom flask and cooled to 0° C. with an ice bath. Water (6.0 mL, 0.332 mol) was added via syringe pump over a 2.0 hour period, then the reaction was allowed to warm to room temperature and stir overnight.

The mixture was extracted with water (150 mL) several times until the aqueous phase was neutral. The methylene chloride was dried with MgSO$_4$, filtered and removed under reduced pressure. The oil was placed under high vacuum at room temperature to remove residual methylene chloride, 11.6 g. (65° C.).

The cyclic silane mixture (10.0 g., 0.167 mol Si-H) and toluene (100 mL) were mixed together in a 250 mL round bottom flask equipped with a Dean-Stark trap, condenser and N$_2$(g) inlet. The solution was azeotropically dried for 2 hours, then cooled to room temperature. The Lamoreaux catalyst (30 mg) was added, then vinyl cyclohexene oxide (22.54 g., 0.183 mol) was added slowly over a 30 minute period. The reaction did not exhibit a dramatic exotherm, however the temperature rose from 23° C. to 28° C. The reaction was stirred for 1 hour at room temperature, then 2 hours at 50° C. to 55° C. (oil bath). After 2 hours (no Si-H was evident in the IR), the reaction was stopped and mercaptobenzothiazole (6 mg.) was added. The toluene was removed under reduced pressure and the excess vinyl cyclohexene oxide was removed under high vacuum. This yielded 25.9 g. of crude product (85%).

EXAMPLE 4

The cyclic epoxy pentamer was prepared by first distilling the cyclic pentamer ($D_5^H$) from an oligomeric distribution of cyclic oligomers (n=3-10) prepared as in Example 3 above, and then hydrosilyating the cyclic pentamer with 3-vinyl-7-oxabicyclo[4.1.0]heptane.

In the examples below, samples for heat distortion temperature (HDT) testing were prepared as follows. The Epon R 825 (bisphenol A diglycidyl ether) was warmed until the material melted, then mixed with the cyclic epoxy siloxane monomer(s). (4-Octyloxyphenyl) phenyliodonium hexafluoroantimonate ("octacat") was then added to the solution with slight warming, followed by the addition of the copper stearate. The resulting mixture was poured into a Teflon mold, which was prewarmed to 80° C. The mold was heated in an oven at 150°-170° C. for a period of approximately 1-2 hours. The samples were slowly cooled to room temperature and then removed from the mold.

COMPARATIVE EXAMPLES A-L

Samples having the compositions set forth in Table 1 were prepared and their heat distortion temperatures measured according to the method described above. The heat distortion temperatures of these samples are set forth in Table 1.

TABLE 1

| | Heat Distortion Temperatures for Cyclic Epoxysiloxane Resins and EPON ® 825. | | | | | |
|---|---|---|---|---|---|---|
| Example No. | Monomer | Octaca$^a$ | Cu(II) | Cure Temp. | Time | HDT |
| A | $D_4^E$ | 0.6% | 0.06% | 170° C.$^a$ | 0.75 hr | 66° C. |
| B | $D_4^E$ | 2.5% | 0.25% | 150° C. | 1.5 hr | 311° C. |
| C | $D_4^E$ | 3.5% | 0.35% | 150° C. | 1.5 hr | — |

TABLE 1-continued

Heat Distortion Temperatures for Cyclic Epoxysiloxane Resins and EPON ® 825.

| Example No. | Monomer | Octaca[a] | Cu(II) | Cure Temp. | Time | HDT |
|---|---|---|---|---|---|---|
| D | $D_n^E$ | 2.5% | 0.25% | 150° C. | 1.5 hr | 294° C. |
| E | $D_4^E$ | 2.5% | 0.25% | 150° C. | 1.5 hr | — |
| F | Epon ® 825 | 0.6% | 0.06% | 120° C.[a] | 1.5 hr | 60° C. |
| G | Epon ® 825 | 1.5% | 0.15% | 120° C.[a] | 1.5 hr | 76° C. |
| H | Epon ® 825 | 2.5% | 0.25% | 120° C.[a] | 1.5 hr | 112° C. |
| I | Epon ® 825 | 2.5% | 0.25% | 150° C. | 0.5 hr | 120° C.[b] |
| J | Epon ® 825 | 3.5% | 0.35% | 170° C. | 0.75 hr | — |
| K | Epon ® 825 | 2.5% | 0.25% | 150° C. | 0.75 hr | 147° C. |
| L | Epon ® 825 | 2.5% | 0.125% | 150° C. | 0.75 hr | 153° C. |

Note: Catalyst quantities were weight percentages and all materials were postcured at 170° C. ([a]no postcure; [b]copper naphthanate was used; —: samples cracked on cooling The data presented in Table 1 indicates that the heat distortion temperatures varied depending upon the monomer. The highest distortion temperatures were recorded for the highly functionalized cyclic oligomer. These monomers, due to their cyclic structure and high degree of functionality, form a cured material with a high crosslink density. Attempts to prepare casting resins of the cyclic pentamer ($D_5^E$) failed when the bars continually cracked upon cooling. This was also observed when higher levels of catalyst (3.5% by weight) were cured with the cyclic tetramer ($D_4^E$).

When the Epon ® 825 bars were cured at 120° C. and no postcure was made, heat distortion temperatures were observed to vary with catalyst level. However, when these resins were postcured at 150° C. in an oven, higher distortion temperatures were obtained and the difference in distortion temperature disappeared.

EXAMPLES 1-7

In Examples 1-7, mixtures of cyclic epoxy siloxane monomers with the bisglycidyl ether of bisphenol A or Epon ® 825 were prepared. All of the mixtures were composed of one-half Epon ® 825 and one-half cyclic epoxysilicone by weight. The samples for HDT tests were prepared as previously described. The results are shown in Table 2 below.

TABLE 2

Heat Distortion Temperatures for Mixtures of Cyclic Epoxysiloxane Resins and Epon ® 825

| Example No. | Monomer | Octacat | Cu(II) | Cure Temp. | Time | HDT |
|---|---|---|---|---|---|---|
| 1 | $D_4^E$ | 2.5% | 0.25% | 150° C. | 0.75 hr | 213° C. |
| 2 | $D_4^E$ | 0.6% | 0.06% | 150° C. | 1.5 hr | 66° C. |
| 3 | $D_n^E$ | 2.5% | 0.25% | 150° C. | 0.75 hr | — |
| 4 | $D_5^E$ | 2.5% | 0.25% | 150° C. | 0.75 hr | — |
| 5 | $M_2^E$ | 2.5% | 0.25% | 150° C. | 0.75 hr | 100° C. |
| 6 | $M_2^E$ | 0.6% | 0.06% | 150° C. | 1.0 hr | 53° C. |
| 7 | $D_2^E D_2$ | 2.5% | 0.25% | 120° C. | 0.75 hr | 111° C. |

Note: Compositions were 1:1 by weight.

The data presented in Table 2 indicates that the heat distortion temperature of an Epon ® 825 polymerized composition is increased if the $D_4^E$ epoxy siloxane monomer is blended with the Epon ® 825 resin in the polymerizable composition. It can also be seen from Table 2 that the heat distortion temperatures for the various mixed resins were consistent with both components. In general, the observed temperatures were the average of the two components. In addition, the same trend with the cyclic epoxysiloxane/Epon ® 825 mixtures were observed. Higher distortion temperatures were recorded for the cyclic monomers than for the linear dimer $M_2^E$ or the difunctional cyclic monomer $D_2^E D_2$. The monomers with higher functionality and higher crosslinking capability had higher distortion temperatures.

Thus, the data provided in Tables 1 and 2 indicates that the heat distortion temperatures vary according to the onium salt catalyst level and the resin composition.

What is claimed is:

1. A heat curable cyclic epoxy siloxane/organic epoxy resin blend which will polymerize to form a composition having a high heat distortion temperature, the blend comprising:

(A) a cyclic epoxy functional siloxane monomer having the general formula

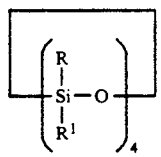

(I)

wherein each R group is, independently, a monovalent substituted or unsubstituted $C_{1-12}$ alkyl, $C_{1-12}$ cycloalkyl, or phenyl radical; each $R^1$ group is, independently, R, or a monovalent epoxy functional group having 2-10 carbon atoms with the proviso that at least one of the R¹ groups is epoxy functional;

(B) an organic epoxy resin, the ratio of parts of (A) to parts (B) being from about 10:1 to about 1:1;

(C) from about 2.5 to about 3.0 weight percent, based on the combined weight of (A) and (B), of a cationic onium salt catalyst having the formula:

$[(R^2)_a(R^3)_b(R^4)_cX]_d^+[MQ_e]^{-(e-f)}$, wherein $R^2$ is a monovalent aromatic organic radical, $R^3$ is a monovalent organic aliphatic radical selected from alkyl, cycloalkyl and substituted alkyl, $R^4$ is a polyvalent organic radical forming a heterocyclic or fused ring structure selected from aliphatic radicals and aromatic radicals, X is a Group VIa element selected from sulfur, selenium and tellurium, M is a metal or metalloid, Q is a halogen radical, a is a whole number equal to 0 to 3 inclusive, b is a whole number equal to 0 to 2 inclusive, c is a whole number equal to 0 or 1 where the sum of a+b+c is a value equal to 3 or the valence of X, d=e−f, f=valence of M and is an integer equal to from 2 to 7 inclusive, e is greater than f and is an integer having a value up to 8; and (D) from about 0.25 to about 0.30 weight percent, based on the combined weight of (A) and (B), of a copper salt cocatalyst selected from Cu(I) halide, Cu(II) benzoate, Cu(II) acetate, Cu(II) stearate, Cu(II) gluconate, Cu(II) citrate, Cu(II) formate, Cu(II) oleate, or Cu(II) carbonate.

2. A composition according to claim 1 wherein R is methyl and R¹ is a monovalent epoxy functional group having 2-10 carbon atoms.

3. A composition according to claim 2 wherein R¹ is has the formula

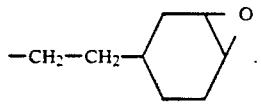

4. A composition according to claim 1 wherein the organic epoxy resin is bisphenol A diglycidyl ether.

5. A composition according to claim 1 wherein the ratio of parts of (A) to parts of (B) is from about 4:1 to about 1:1.

6. A composition according to claim 5 wherein the ratio of parts of (A) to parts of (B) is about 1:1.

7. A composition according to claim 1 wherein the onium salt catalyst is present in the amount of about 2.5% based on the combined weight of (A) and (B).

8. A composition according to claim 1 wherein the copper cocatalyst is present in the amount of about 0.25% based on the combined weight of (A) and (B).

9. A composition according to claim 1 wherein the onium salt catalyst is a diaryliodonium salt having the formula:

$[(R^2)_a(R^3)_b(R^4)_cX]_d^+[MQ_e]^{-(e-f)}$, wherein $R^2$ is a monovalent aromatic organic radical, $R^3$ is a monovalent organic aliphatic radical selected from alkyl, cycloalkyl and substituted alkyl, $R^4$ is a polyvalent organic radical forming a heterocyclic or fused ring structure selected from aliphatic radicals and aromatic radicals, X is a Group VIa element selected from sulfur, selenium and tellurium, M is a metal or metalloid, Q is a halogen radical, a is a whole number equal to 0 to 3 inclusive, b is a whole number equal to 0 to 2 inclusive, c is a whole number equal to 0 or 1 where the sum of a+b+c is a value equal to 3 or the valence of X, d=e−f, f=valence of M and is an integer equal to from 2 to 7 inclusive, e is greater than f and is an integer having a value up to 8.

10. A composition according to claim 9 wherein the onium salt catalyst is (4-octyloxyphenyl) phenyliodonium hexafluoroantimonate.

11. A composition according to claim 1 wherein the copper salt is copper stearate.

12. A heat curable cyclic epoxy siloxane/organic epoxy resin blend which will polymerize to form a composition having a high heat distortion temperature, the blend comprising:

(A) a tetramethyltetraepoxy cyclic siloxane monomer having the formula

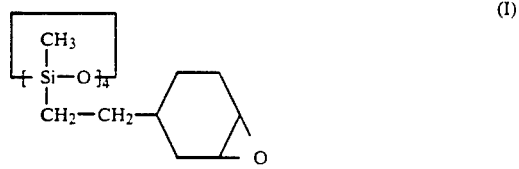

(B) bisphenol A diglycidyl ether, wherein the ratio of parts of (A) to parts of (B) is about 1:1;

(C) about 2.5 weight percent, based on the combined weight of (A) and (B), of (4-octyloxyphenyl) phenyliodonium hexafluoroantimonate; and (D) about 0.25 weight percent, based on the combined weight of (A) and (B), of cupric stearate.

13. The polymerized composition of claim 1.

14. The polymerized composition of claim 12.

15. A method of preparing an epoxy siloxane/organic epoxy composition having a high heat distortion temperature, comprising the step of thermally polymerizing a mixture of ingredients comprising:

(A) a cyclic epoxy functional siloxane monomer having the general formula

wherein each R group is, independently, a monovalent substituted or unsubstituted $C_{1-12}$ alkyl, $C_{1-12}$ cycloalkyl, or phenyl radical; each R¹ group is, independently, R, or a monovalent epoxy functional group having 2-10 carbon atoms with the proviso that at least one of the R¹ groups is epoxy functional;

(B) an organic epoxy resin, the ratio of parts of (A) to parts of (B) being from about 10:1 to about 1:1;

(C) from about 2.5 to about 3.0 weight percent, based on the combined weight of (A) and (B), of a cationic onium salt catalyst having the formula:

$[(R^2)_a(R^3)_b(R^4)_cX]_d^+[MQ_e]^{-(e-f)}$, wherein $R^2$ is a monovalent aromatic organic radical, $R^3$ is a monovalent organic aliphatic radical selected from alkyl, cycloalkyl and substituted alkyl, $R^4$ is a polyvalent organic radical forming a heterocyclic or fused ring structure selected from aliphatic radicals and aromatic radicals, X is a Group VIa element selected from sulfur, selenium and tellurium, M is a metal or metalloid, Q is a halogen radical, a is a whole number equal to 0 to 3 inclusive, b is a whole number equal to 0 to 2 inclusive, c is a whole number equal to 0 to 1 where the sum of $a+b+c$ is a value equal to 3 or the valence of X, $d=e-f$, $f=$ valence of M and is an integer equal to from 2 to 7 inclusive, e is greater than f and is an integer having a value up to 8; and (D) from about 0.25 to about 0.30 weight percent, based on the combined weight of (A) and (B), of a copper salt cocatalyst selected from Cu(I) halide, Cu(II) benzoate, Cu(II) acetate, Cu(II) stearate, Cu(II) gluconate, Cu(II) citrate, Cu(II) formate, Cu(II) oleate, or Cu(II) carbonate.

* * * * *